United States Patent
Valmier

(10) Patent No.: US 10,709,687 B2
(45) Date of Patent: Jul. 14, 2020

(54) FLT3 RECEPTOR INHIBITOR AT LOW DOSAGE FOR THE TREATMENT OF NEUROPATHIC PAIN

(71) Applicants: INSTITUT NATIONAL DE LA SANTE ET DE LA RECHERCHE MEDICALE (INSERM), Paris (FR); UNIVERSITE DE MONTPELLIER, Montpellier (FR); BIODOL THERAPEUTICS, Clapiers (FR)

(72) Inventor: Jean Valmier, Saint Georges d'Orques (FR)

(73) Assignees: INSERM (INSTITUT NATIONAL DE LA SANTÉ ET DE LA RECHERCHE MÉDICALE), Paris (FR); UNIVERSITE DE MONTPELLIER, Montpellier (FR); BIODOL THERAPEUTICS, Clapiers (FR)

( * ) Notice: Subject to any disclaimer, the term of this patent is extended or adjusted under 35 U.S.C. 154(b) by 0 days.

(21) Appl. No.: 16/307,968

(22) PCT Filed: Jun. 8, 2017

(86) PCT No.: PCT/EP2017/063935
§ 371 (c)(1),
(2) Date: Dec. 7, 2018

(87) PCT Pub. No.: WO2017/211937
PCT Pub. Date: Dec. 14, 2017

(65) Prior Publication Data
US 2019/0298691 A1    Oct. 3, 2019

(30) Foreign Application Priority Data

Jun. 8, 2016 (EP) .................................. 16305669

(51) Int. Cl.
*A61K 31/404* (2006.01)
*A61P 25/02* (2006.01)
*A61P 29/00* (2006.01)
*A61K 9/00* (2006.01)
*A61K 9/70* (2006.01)
*A61K 31/497* (2006.01)
*A61K 31/5377* (2006.01)
*A61K 31/553* (2006.01)
*A61K 31/44* (2006.01)

(52) U.S. Cl.
CPC .......... *A61K 31/404* (2013.01); *A61K 9/0053* (2013.01); *A61K 9/7023* (2013.01); *A61K 31/44* (2013.01); *A61K 31/497* (2013.01); *A61K 31/5377* (2013.01); *A61K 31/553* (2013.01); *A61P 25/02* (2018.01); *A61P 29/00* (2018.01)

(58) Field of Classification Search
CPC .............................. A61K 31/404; A61P 25/02
USPC ....................................................... 514/211.8
See application file for complete search history.

(56) References Cited

FOREIGN PATENT DOCUMENTS

| WO | WO-2011083124 A1 * | 7/2011 | ......... C12N 15/1138 |
|---|---|---|---|
| WO | WO-2016016370 A1 * | 2/2016 | ........... C07D 233/64 |

* cited by examiner

*Primary Examiner* — Kevin E Weddington
(74) *Attorney, Agent, or Firm* — W&C IP

(57) ABSTRACT

The present invention relates to FLT3 receptor inhibitor for use in the treatment of neuropathic pain and chronic pain comprising a neuropathic component, wherein the daily dosage range per human adult per day of said FLT3 receptor inhibitor consists of a dosage range determined by a method comprising the steps of: (i) determining the minimal inhibiting dose of said FLT3 receptor inhibitor that induces the maximal inhibition of mechanical pain hypersensitivity, (ii) converting said dose to the Human Equivalent Dose (HED) by the allometric correction method, and (iii) establishing a daily dosage range per human adult per day wherein (iii-1) the lower limit of the said daily dosage range per human adult per day is the greater value between HED/20 determined via a rat model and 0.001 mg, and (iii-2) the upper limit of the said daily dosage range is the lower value between HED*20 determined via a rat model and 50 mg.

29 Claims, 2 Drawing Sheets

FLT3 RECEPTOR INHIBITOR AT LOW DOSAGE FOR THE TREATMENT OF NEUROPATHIC PAIN

FIELD OF THE INVENTION

The present invention relates to FLT3 receptor inhibitors for use in the treatment of neuropathic pain and chronic pain comprising a neuropathic component.

The present invention more particularly concerns the use of low amounts, in particular low daily dose per human adult, of such FLT3 receptor inhibitors, in the treatment of neuropathic pain and chronic pain comprising a neuropathic component.

BACKGROUND OF THE INVENTION

Neuropathic pain, refers to a pain that occurs after nerve injury or a disease of the somatosensory system, is a debilitating chronic clinical condition, one hallmark symptom of which is tactile hypersensitivity to pain. Although acute pain (duration <3 months) can be efficiently controlled by a large arsenal of various drugs, such as non-steroid anti-inflammatory drugs (NSAIDs) or opioids for severe cases, the current treatment of chronic pain (duration >3 months), especially neuropathic pain, is essentially symptomatic and unsatisfactory for most patients. Indeed, a number of pain medications are available on the pharmaceutical market, most of which have been initially marketed for other indications, e.g. epilepsy and depression. These medications are however only partially efficacious against neuropathic pain: only a limited number of patients achieve a 50% reduction of their pain symptoms and it is still today unfortunately observed that some neuropathic pain syndromes are completely refractory to these medications, thus affecting considerably the quality of life of these patients (Finnerup et al., Lancet Neurol. 2015, 14:162-173). Moreover, the existing medications often generate a large variety of adverse effects that limit their use in patients: they can elicit dizziness, somnolence, tiredness, constipation, dry mouth, nausea, vomiting, and weight gain.

FLT3 is a member of the class III receptor tyrosine kinase (RTK) family which comprises stem cell factor (SCF) receptor (c-kit), colony-stimulating factor type-I (CSF-1) receptor (c-fms) and platelet-derived growth factor (PDGF) receptor (PDGFR). FLT3, like other RTKs, is a transmembrane receptor, which contains an extracellular domain interacting with its ligand FL, and an intracellular domain containing a kinase domain responsible of auto-phosphorylation. Upon activation, FLT3 dimerizes and auto-phosphorylates tyrosine residues present in its intracellular domain. FLT3 is predominantly expressed in the human lympho-hematopoietic system, which generates blood cells. FL/FLT3 signaling regulates proliferation, survival and differentiation of hematopoietic/progenitor cells and can lead to the differentiation of progenitors into dendritic cells. Mutations in FLT3 responsible for auto-activation have been identified in up to 30% of acute myeloid leukemia (AML) patients, worsening the prognostic.

Indeed, FLT3 receptor inhibitors were initially known for their use in the treatment of cancer. Small molecule kinase inhibitors (Receptor Tyrosine Kinase Inhibitors; RTKI) are recognized drugs that have been intended to treat human patients with various cancers, some of them being already marketed for oncology indications, in AML and other malignant diseases in which FLT3 activation is implicated. These compounds act via blocking the intracellular kinase domain of the receptor tyrosine. They inhibit FLT3 in cellular assays and are also efficacious in mouse models of these cancerous pathologies. In phase 1 and phase 2 clinical trials, conducted primarily in relapsed or refractory AML patients, clinical responses were consistently observed with these drugs.

In contrast to FLT3, FL is expressed in most human tissues and in blood. FLT3 expression has been also identified in the nervous system (Rosney et al. *Oncogene;* 1991, 6, 1641-1650). The only known role of FL/FLT3 interactions on neuron functioning on the somato-sensory system is the developmental regulation of neural stem cells proliferation and a synergistic effect with nerve growth factor (NGF) promoting early embryonic DRG sensory neuron survival in vitro.

Moreover, it is known from document WO2011/083124 to use a FLT3 receptor inhibitor for the treatment of pain disorders. Neuropathic pain is cited among a large list of pain disorders that encompasses acute pain, chronic pain, neuropathic pain, inflammatory pain, low back pain, post-operative pain, cancer pain, vascular headache such as migraine, fibromyalgia, hyperalgesia such as mechanical ant thermal hyperalgesia, allodynia such as thermal and mechanical allodynia, peripheral sensitization of pain mechanisms and central sensitization of pain mechanisms.

However, said document is silent on which specific pain disorders that can be treated with an FLT3 receptor inhibitor and on specific daily dosages of said FLT3 receptor inhibitor aiming at specifically dealing with a particular pain disorder. WO2011/083124 discloses the possibility of dosages of an FLT3 receptor inhibitor for treating a pain disorder in the range of 0.1 to 50 mg, which is a range too large to be adapted to a particular pain disorder and to avoid side-effects, particularly on long-term use needed for chronic pain.

Indeed, at doses used for the treatment of different cancer diseases, FLT3 receptor inhibitors generate numerous and often serious (grade 3, 4) adverse events. These include frequent adverse reactions such as fatigue, asthenia, fever, diarrhea, nausea, mucositis/stomatitis, vomiting, dyspepsia, abdominal pain, constipation, hypertension, peripheral edema, rash, skin disorders. Potentially serious adverse reactions such as hepatotoxicity, left ventricular dysfunction, congestive heart failure, QT interval prolongation, hemorrhage, hypertension, thyroid dysfunction, pancreatitis, and adrenal function have also been observed (Terada et al., Pharmacology & Therapeutics, 2015, 152: 125-134; Gathalia et al., Critical Rev in Oncol/Hematol, 2015, 93:257-276; ibid, Critical Rev in Oncol/Hematol, 2015, 94: 136-145; ibid, Critical Rev in Oncol/Hematol, 2015, 94: 228-237; ibid, British Journal of Cancer, 2015, 112:296-305; Youjin et al., Lancet Oncol 2009; 10: 967-74; Massey et al., Support Care Cancer, 2015, 23:1827-1835; Santoni et al., Int J Cancer. 2014, 135:763-773).

In particular, there is a continuing need for providing the skilled person with means for treating patients suffering from neuropathic pain and chronic pain comprising a neuropathic component, for which limited treatments are currently available as reminded above, and at low daily dosage for long-term treatment, in particular with sufficient efficiency and for avoiding the occurrence of aforementioned adverse effects.

Because different pain disorders may proceed from distinct mechanisms, there is an additional need to provide the skilled person with efficient drugs for treating patients suffering from neuropathic pain and chronic pain comprising a neuropathic component addressing the cause and not only the consequences of the disease in adapted daily dosages, in particular minimum daily dosages, for avoiding the occurrence of adverse effects as reminded above.

The present invention has for purpose to meet these needs.

SUMMARY OF THE INVENTION

Unexpectedly, the inventor has found that FLT3 receptor inhibitors are active against neuropathic pain, but not on pain arising from a distinct etiology, such as inflammatory pain as illustrated in example 1 herein after. Moreover, FLT3 receptor antagonists act in vitro on FLT3 in the nociceptive system responsible for neuropathic pain, at concentrations much lower than the concentrations necessary for inhibiting FLT3 and proliferation in tumoral cells. Moreover, the inventor found that the doses for inhibiting neuropathic pain in a rat model were much lower than the antitumoral doses needed in animals, or their equivalent doses in human patients with cancers.

Therefore, the present invention concerns FLT3 receptor inhibitor for specific use in the treatment of neuropathic pain and chronic pain comprising a neuropathic component, wherein the daily dosage range per human adult per day of said FLT3 receptor inhibitor consists of a dosage range determined by a method comprising the steps of:
- (i) determining the minimal inhibiting dose of said FLT3 receptor inhibitor that induces the maximal inhibition of mechanical pain hypersensitivity in a model of nerve injury, which is the Spinal Nerve Ligation (SNL) Model in rats,
- (ii) converting said dose to the Human Equivalent Dose (HED) by the allometric correction method, the daily dose being calculated as the daily dose for a human with a body weight of 60 kg, and
- (iii) establishing a daily dosage range per human adult per day wherein
  - (iii-1) the lower limit of the said daily dosage range per human adult per day is the greater value between HED/20 determined via the SNL rat model and 0.001 mg, and
  - (iii-2) the upper limit of the said daily dosage range is the lower value between HED*20 determined via the SNL rat model and 50 mg.

In the context of the present invention:
The terms "FLT3" or "FLT3 receptor" (fms-related tyrosine kinase 3), also known as the CD135, Ly72, Flk-2, Flt-3 or B230315G04, are used interchangeably and have their general meaning in the art. The FLT3 receptor can be from any source, but typically is a mammalian (e.g., human and non-human primate) FLT3 receptor, particularly a human FLT3 receptor.

The terms "FL" or "FLT3-Ligand" are used interchangeably and have their general meaning in the art. They refer to the cytokine which is a natural ligand of the FLT3 receptor. FL can be from any source, but typically is a mammalian (e.g., human and non-human primate) FL, particularly a human FL. By "receptor inhibitor" is meant a natural or synthetic compound that has a biological effect opposite to that of a receptor agonist.

The terms "FLT3 receptor inhibitor" includes any synthetic or biological entity that has a biological effect opposite to that of a receptor agonist and can block FLT3 receptor activation or can act by inhibiting the kinase activity of the receptor tyrosine kinase. Such FLT3 receptor inhibitors in particular include any entity that significantly inhibits at a concentration of 1 μM or less, FLT3 auto-phosphorylation of any of the tyrosines present in the intracellular domain of FLT3, identified as the sequence aminoacids 564 to 993 (Swissprot P36888), in particular of tyrosines 572, 589, 591, 599, 726, 768, 793, 842, 955 and 969.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5,000 Da, more preferably up to 1,000 Da, and most preferably up to about 500 Da.

the term "patient" or a "subject" may extend to humans or mammals, such as rodents, felines, cats, dogs, horses and primates. Preferably a "patient" or a "subject" according to the invention is a human adult.

In its broadest meaning, the term "treating" or "treatment" refers to reversing, alleviating, inhibiting the progress of, or preventing the disorder or condition to which such term applies, or one or more symptoms of such disorder or condition.

"Pharmaceutically" or "pharmaceutically acceptable" refers to molecular entities and compositions that do not produce an adverse, allergic or other untoward reaction when administered to a mammal, especially a human, as appropriate.

The terms "between . . . and . . . " and "ranging from . . . to . . . " should be understood as being inclusive of the limits, unless otherwise specified.

DETAILED DESCRIPTION OF THE INVENTION

Figure 1:
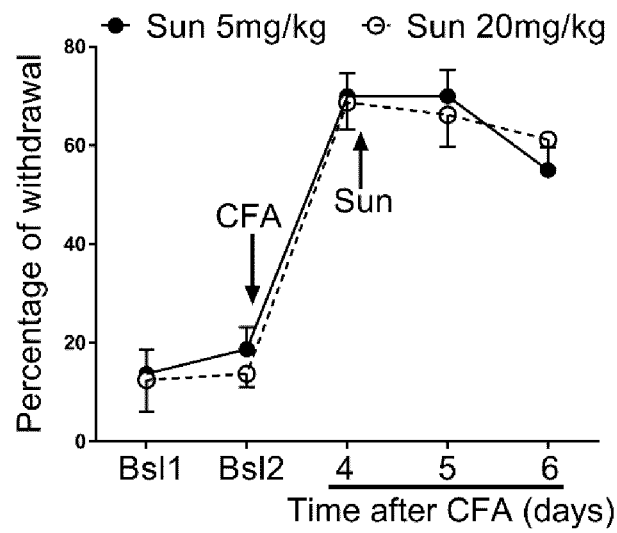
FIG. 1 shows that the FLT3 inhibitor sunitinib is inactive on pain hypersensitivity in a model of inflammatory pain as illustrated in example 1.

The present invention has for purpose to meet the aforementioned needs.

FLT3 Receptor Inhibitor

According to a particular embodiment, the FLT3 receptor inhibitor is a low molecular weight molecule, e.g. a small organic compound.

Exemplary FLT3 receptor inhibitors that are contemplated by the invention include but are not limited to those described in Sternberg et al. 2004 and in International Patent Application WO 2002/032861, WO 2002/092599, WO 2003/035009, WO2003/024931, WO 2003/037347, WO 2003/057690, WO 2003/099771, WO 2004/005281, WO 2004/016597, WO 2004/018419, WO 2004/039782, WO 2004/043389, WO 2004/046120, WO 2004/058749, WO 2004/058749, WO 2003/024969, WO 2006/138155, WO 2007/048088 and WO 2009/095399 which are incorporated herein by reference.

Examples of FLT3 receptor inhibitors that are contemplated include AG1295 and AG1296; Lestaurtinib (also known as CEP-701, formerly KT-5555, Kyowa Hakko, licensed to Cephalon); CEP-5214 and CEP7055 (Cephalon); CHIR-258 (Chiron Corp.); GTP (Merk Biosciences UK); Midostaurin (also known as PKC 412, Novartis AG); quizartinib (AC 220); gilteritinib (Koltobuki/Astellas Pharma); Semaxinib (Sugen); Linifanib (Roche/Genetech/Abbvie); Fostamatinib (Rigel); Pexidartinib (Plexxikon/Daiichi Sanyo); Sorafenib (Nexavar®, Bayer Schering Pharma Ag); Cabozantinib (Cometriq®, Swedish Orphan Biovitrum); Ponatinib (Iclusig®, Ariad Pharmaceuticals); Ilorasertib (ABT-348); Pacritinib; Famitinib; MLN-608 (Millennium USA); MLN-518 (formerly CT53518, COR Therapeutics Inc., licensed to Millennium Pharmaceuticals Inc.); MLN-608 (Millennium Pharmaceuticals Inc.); sunitinib (SU-11248, or Sutent®, Pfizer, USA); SU-11657 (Pfizer, USA); SU-5416 and SU-5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA).

According to a preferred embodiment, the FLT3 receptor inhibitor is preferably a selective FLT3 receptor inhibitor.

Indeed, in the context of the present invention, when FLT3 receptor inhibitors are small organic molecules, said inhibitors are preferably selective for the FLT3 receptor as compared with the other tyrosine kinase receptors, such as c-Kit receptor.

By "selective" it is meant that the affinity of the inhibitor for the FLT3 receptor is at least 10-fold, preferably 25-fold, higher than for the other tyrosine kinase receptors, e.g. c-Kit receptor. Selectivity of a FLT3 receptor inhibitors may be assayed for instance by carrying out biochemical kinase binding assays such as KinomeScan kinase binding assays as described in Sternberg et al. (Curr Opin Hematol, 2005, 12:7-13) and in International Patent described in Fabian et al. (Nat Biotechnol, 2005 23/329-336) and Karaman et al. (Nat Biotechnol, 2008, 26:127-132). For the FLT3 assay, a kinase construct that spanned the catalytic domain and is designed to measure the intrinsic binding affinity of the open FLT3 active site for inhibitors as previously described in Zarrinkar et al. (Blood. 2009, 114:2984-2992).

Exemplary selective FLT3 receptor inhibitors that are contemplated by the invention include but are not limited to those described in Zarrinkar et al. (Blood. 2009, 114:2984-2992) and in International Patent Applications No WO 2007/109120 and WO 2009/061446 which are incorporated herein by reference.

The FLT3 receptor inhibitor as used in the framework of the present invention may also consist of a mixture of said previously cited FLT3 receptor inhibitors.

According to a further embodiment, the FLT3 receptor inhibitor is selected among sunitinib, quizartinib, gilteritinib and midostaurin.

According to a further embodiment of the present invention, the said inhibitor is administered under the form of a free base or a pharmaceutically acceptable addition salt thereof.

Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Neuropathic Pain and Chronic Pain Comprising a Neuropathic Component

According to the definition by The International Association for the Study of Pain (Treede et al., Neurology, 2008, 70:1630-1635), the term "neuropathic pain" refers to a chronic or persisting pain disorder, arising as a direct consequence of a lesion or disease affecting the somatosensory system, which includes the nociceptive system and its ascending and descending pathways. The term lesion is commonly used when diagnostic investigations (e.g. clinical investigations imaging, neurophysiology, biopsies, lab tests) reveal an abnormality or when there was obvious trauma. The term disease is commonly used when the underlying cause of the lesion is known (e.g. stroke, vasculitis, diabetes mellitus, genetic abnormality). The symptoms include hyperalgesia, i.e. from a stimulus that normally provokes pain, and allodynia, i.e. pain due to a stimulus that does not normally provoke pain.

Neuropathic pain can be either peripheral or central neuropathic pain, based on the anatomic location of the lesion or disease. However, the distribution of pain or hyperalgesia is not necessarily identical to the innervation territory of the organ affected by the disease.

According to a particular embodiment of the present invention, neuropathic pain, which may also be called neuropathic pain syndrome, is selected from pain arising from metabolic diseases, for example painful diabetic neuropathic pain, infectious diseases, for example post-herpetic neuralgia, trigeminal neuralgia, post-traumatic neuropathic pain, lumbosacral radiculopathic pain, post-chirurgical neuropathic pain, iatrogenic neuropathic pain, for example chemotherapy-based neuropathic pain, and central neuropathic pain.

Neuropathic pain is distinct from inflammatory pain, which is produced by localized reaction following a damage to tissues outside the sensory system, for instance joints, ligaments, tendons, bones, muscles, blood vessels or visceral structures. Unexpectedly, the inventor found that inflammatory pain, as assessed in the well-known Complete Freund's Adjuvant (CFA) animal model (Fehrenbacher et al., Curr Protoc Pharmacol. 2012 March; Chapter 5:Unit5.4. doi: 10.1002/0471141755.ph0504s56.) is insensitive to an FLT3 receptor inhibitor, at doses that are active against neuropathic pain and even at a higher dose (Example 1, FIG. 1). This emphasizes the need of precisely defining the doses of FLT3 inhibitors to be used for treating neuropathic pain.

Neuropathic pain can coexist with other types of pain, and in particular in chronic pain. Therefore, as used herein, a "chronic pain comprising a neuropathic component" means a chronic pain in which a type of pain different from neuropathic pain, for instance inflammatory or nociceptive pain, coexists with a neuropathic pain.

Thus, according to a further particular embodiment of the present invention, the chronic pain comprising a neuropathic component is selected from low-back pain, osteoarthritic pain, cancer pain, sciatica.

DAILY DOSES and REGIMENS

The present invention relates to FLT3 receptor inhibitor for use in the treatment of neuropathic pain and chronic pain comprising a neuropathic component, wherein the daily dosage range per human adult per day of said FLT3 receptor inhibitor consists of a dosage range determined by a method (Method 1) comprising the steps of:
(i) determining the minimal inhibiting dose of said FLT3 receptor inhibitor that induces the maximal inhibition of Spinal Nerve Ligation-induced mechanical hypersensitivity in a model of nerve injury, which is the Spinal Nerve Ligation Model in rats, (ii) converting said dose to the Human Equivalent Dose (HED) by the allometric correction method, the daily dose being calculated as the daily dose for a human with a body weight of 60 kg, and (iii) establishing a daily dosage range per human adult per day wherein (iii-1) the lower limit of the said daily dosage range per human adult per day is the greater value between HED/20 determined via the SNL rat model and 0.001 mg, and (iii-2) the upper limit of the said daily dosage range is the lower value between HED*20 determined via the SNL rat model and 50 mg.

It is shown in the examples herein after that FLT3 receptor inhibitors are much more potent in vitro to inhibit FLT3 activation in the pain system than in tumor cells (Example 2), and in vivo to inhibit neuropathic pain than to elicit tumor regression (Examples 3).

The FLT3 inhibitor sunitinib was thus evaluated in the following experimental part in neuropathic pain in rats.

The efficacy of an inhibitor for FLT3 receptor may classically be quantified by measuring the inhibition of FLT3 receptor activation in the presence of a range of concentrations of said inhibitor in order to establish a dose-response curve. From that dose response curve, a concentration inhibiting 50% of the activity ($IC_{50}$) value may be deduced which represents the concentration of inhibitor necessary to inhibit 50% of the response to an agonist in defined concentration.

As an example of the high in vitro potency of FLT3 inhibitors on the pain system, the potency of the FLT3 receptor inhibitor sunitinib was evaluated in preparations of Dorsal Root Ganglia ganglia (DRG), an essential structure for pain transmission, as described in WO 201183124. It was found that $IC_{50}$ value of sunitinib was 0.70 nM (Example 2, FIG. 2). In comparison, the $IC_{50}$ value for inhibiting FLT3 phosphorylation in leukemia cell lines RS; 411, which express wild-type FLT3 was 250 nM and its IC50 value for inhibiting FLT3-ITD in MV4; 11 cells, which express a mutated form of FLT3 relevant for leukemia, was 50 nM (O'Farrell et al., Blood 2003, 101:3597-3605).

However, according to the present invention, the neuropathic model on rats is mainly used for determining the minimal dose of the active molecule for achieving the inhibition of pain sensitivity as it will be more explicit herein after.

As it is much more detailed herein after, the rat model was chosen as a reference model when characterizing the minimal daily dosage per day in comparison to the active dose for treating cancer or the minimum inhibiting dose inducing maximal tumor regression.

Thus, Example 3 demonstrates that the inhibition of pain sensitivity in SNL model in rats was achieved with a FLT3 receptor inhibitor, and namely sunitinib, at doses drastically lower than the doses for achieving tumor regression.

Thus, in rats, oral administration of Sunitinib (0.15 mg/kg) reversed the mechanical hypersensitivity induced by nerve injury in the SNL model in rats (Example 3). Conversely, oral administration of vehicle had no effect on paw withdrawal responses to mechanical stimulation (Example 3, FIG. 3). A complete dose-response relationship was established for sunitinib in the SNL model in rats. Maximal inhibition of neuropathic pain was achieved with sunitinib doses as low as 0.075 mg/kg by oral administration (Example 3, FIG. 4).

Thus, the dose of sunitinib producing a maximal effect in rats on neuropathic pain is 266-fold lower than the dose inducing maximal tumor regression in mice, which is 20 mg/kg (O'Farrell et al., Blood 2003, 101:3597-3605).

The details of the dosage range determination according to Method 1 with steps (i), (ii) and (iii) as set forth in the claimed invention are given herein after, as well as the encompassed variants.

According to the present invention, doses are expressed as a free base of the FLT3 receptor inhibitor. In other words, even if the considered receptor inhibitor is a pharmaceutically acceptable salt of a small molecule, the daily doses are expressed on the bases of the corresponding small molecule free base.

Step (i)

The chronic Spinal Nerve Ligation model, which involves a tight ligation of the L5 and/or L6 spinal nerves with silk thread as previously described in Kim and Chung (Pain, 1992, 50: 355-363 is a model on rat, illustrated in Example 3 herein after, well known to the man skilled in the art.

In the framework of the present invention, the "minimal inhibition dose of FLT3 receptor inhibitor that induces the maximal inhibition of Spinal Nerve Litigation-induced mechanical hypersensitivity on rat refers to the minimal dose of drug above which the inhibition of pain sensitivity no more increases.

Figure 3:
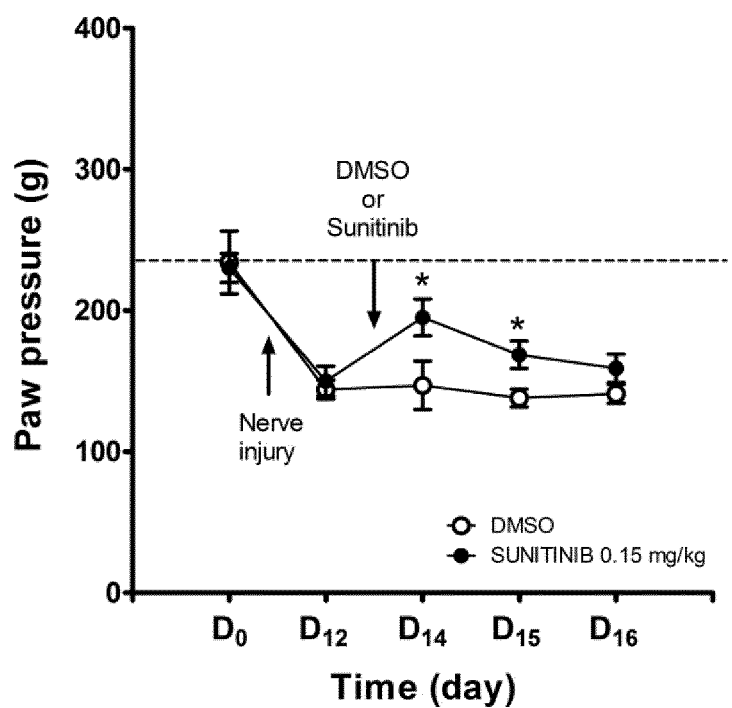
FIG. 3 depicts the paw pressure after sunitinib administration at a dose of 0.15 mg/kg, performed in a nerve injury-induced mechanical pain hypersensitivity in rat (SNL model) as performed in example 3.

As an illustration, Example 3 for sunitinib may be used. Indeed, as set forth in the results part of Example 3, it is concluded that the minimal inhibition dose of sunitinib that induces the maximal inhibition is 0.075 mg/kg (FIG. 3).

Step (ii)

Conversion of the dose as obtained in step (i) to the Human Equivalent Dose (HED) is also a known operation for the man skilled in the art. An appropriate guidance may come from "Guidance for Industry—Estimating the Maximum Safe Starting Dose in Initial Clinical Trials for Therapeutics in Adult Healthy Volunteers U.S. Department of Health and Human Services" from the Food and Drug Administration (FDA) Center for Drug Evaluation and Research (CDER) (July 2005) (http://www.fda.gov/cder/guidance/index.htm).

According to a particular embodiment, the method to estimate the HED from an active dose in animals is based on the allometric correction (US Food and Drug Administration's Guidance for Industry—Estimating the Maximum Safe Starting Dose in Initial Clinical Trials for Therapeutics in Adult Healthy Volunteers, July 2005, available at htt://www.fda.gov/downloads/Drugs/GuidanceCompliance-RegulatoryInformation/Guidances/UCM078932.pdf).

Typically, the allometric FDA factor for the rat is 6.2 and the allometric FDA factor for the mouse is 12.3.

The HED are typically calculated as the daily dose for a human with a body weight of 60 kg.

As an illustrative conversion for the rat dose to HED according to step (ii), example 3, and more particularly FIG. 3 may be used. Indeed, as set forth in the results part of example 3, it is concluded that the maximal inhibition was obtained with sunitinib doses at 0.075 mg/kg and higher.

The HED value may be determined by the following calculation:

$$\text{HED} = 0.075/6.2(\text{allometric FDA factor for the rat}) * 60(\text{weight}) = 0.73 \text{ mg}.$$

Step (iii)

Said last step allows establishing the daily dosage range per human adult per day. The lower limit is the greater value between HED/20 and 0.001 mg and the upper limit is the lower value between HED*20 and 50 mg.

As an illustration, taking into account the data in the rat, the lower limit in the case of sunitinib is the greater value between HED/20=0.037 mg and 0.001 mg, i.e. 0.037 mg and the upper limit is the lower value between HED*20=14.6 mg and 50 mg, i.e. 14.6 mg. As a conclusion, the daily dosage per day per human for sunitinib for the treatment of neuropathic pain and chronic pain comprising a neuropathic component according to the present invention ranges from 0.037 mg to 14.6 mg.

Said step (iii) may also comprise a step of adjusting the dose with respect to the final administration route if said final administration route is different from the oral route by applying to the daily dosage range as obtained in step (iii) a corrective factor in order to obtain the corresponding dose for the considered route of administration. Said adjusting step is well known to the man skilled in the art.

According to a further particular embodiment, the lower limit of the said daily dosage range per human adult per day is the greater value between HED/10 and 0.002 mg and the upper limit of the said daily dosage range is the lower value between HED*10 and 25 mg, and even more particularly the lower limit of the said daily dosage range per human adult per day is the greater value between HED/5 and 0.0025 mg and the upper limit of the said daily dosage range is the lower value between HED*5 and 20 mg.

As an illustration with the case of sunitinib, HED/10=0.073 mg, HED*10=7.3 mg; and HED/5=0.15 mg, HED*5=3.6 mg.

According to another particular embodiment (Method 2), the upper limit of the daily dosage range per human adult per day of the said FLT3 receptor inhibitor is the lower value between the upper limit as determined above in step (iii) and one of
(a) a quarter of the active daily dosage per human adult of the said FLT3 receptor inhibitor used for the treatment of any type of cancer, or
(b) a quarter of the daily dose per human adult of the said FLT3 receptor inhibitor for the treatment of cancer, said daily dose being determined by a method comprising the steps of:
  (i) determining the minimum inhibiting dose inducing maximal tumor regression in a mouse xenograft model sensitive to FLT3 inhibition, and
  (ii) converting said dose to the Human Equivalent Dose (HED) by the allometric correction method, the daily dose being calculated as the daily dose for a human with a body weight of 60 kg.

According to the present invention, Method 1 is generally preferred in comparison to Method 2.

According to a further embodiment, the active daily dosage per human adult of the said FLT3 receptor inhibitor used for the treatment of any type of cancer as used in method 1 is the highest known active daily dosage when various active dosages are known for different cancers.

Active doses for FLT3 receptor inhibitor, according to Method 1 as described above, are the recommended doses, as appearing in the drug label when the product is marketed. Alternatively, when the product is not marketed yet, the active doses are those used in clinical trials and that have demonstrated clinical efficacy against cancer. Such information may be found via various sources well known by the man skilled in the art, such as articles, FDA data publications, labeling of marketed products, Summary of Product Characteristics (SmPC) from the European Medicine Agency (EMA), clinical trial descriptions from the US National Institute of Health (available at www.clinicaltrials.gov) and information on the outer product packaging.

As an illustration of said characterization of the upper limit of the desired daily dosage range per human adult through Method 1 as described above, through recommended daily dosage per human adult of the said FLT3 receptor inhibitor for the treatment of any type of cancer, example of sunitinib may be taken.

Thus, in patients with gastrointestinal stromal tumor (GIST) or metastatic renal cell carcinoma (RCC), the recommended clinical daily dose of sunitinib is 50 mg, whereas in patients with primitive neuroectodermal tumor (pNET), the recommended clinical daily dose of sunitinib is 37.5 mg (Sutent® label, available at http://www.accessdata.fda.gov/drugsatfdadocs/label/2015/021938s0311bl.pdf).

When dividing such doses by four gives a dose of 12.5 mg, which corresponds to the desired upper limit of the daily dosage range per human adult per day of the said FLT3 receptor inhibitor.

Still according to said particular embodiment, and in the framework of the implementation of Method 1 as described above, it may be relevant to characterize the daily dosage per human adult for the treatment of neuropathic pain and chronic pain comprising a neuropathic component in comparison to the active dose for treating cancer starting from the minimal dose for inhibition of pain sensitivity both in the SNL model in rats.

Said approach may be applied to sunitinib.

As determined in the SNL model in rats, HED is 0.73 mg (see above), which is equal to the dose of 50 divided by 68.

Thus the HED of sunitinib to maximally inhibit neuropathic pain is 68 times lower than the doses prescribed in patients with cancer.

Thus, according to a further more particular embodiment of the present invention, the FLT3 receptor inhibitor is sunitinib and the daily dosage per human adult is 68 times lower than the recommended dose for treating cancer, and for example for treating gastrointestinal stromal tumor or metastatic renal cell carcinoma, which is 50 mg.

Alternatively, for some FLT3 receptor inhibitors which are not marketed yet or for which an efficacious dose for treating cancers in humans has not been established, another method may be used to determine the minimum inhibiting dose inducing maximal tumor regression: Method 2 as described above.

The dose of FLT3 receptor inhibitor that induces tumor regression in animal models can be measured by using a mouse xenograft model, which is sensitive to FLT3 inhibition. Such a model may consist in an athymic immunodeficient mouse implanted with human tumor cells that express a mutated, spontaneously activated, form of FLT3. A known mutated form of FLT3 is FLT3-ITD, which results from internal tandem duplications and has been found in patients with AML (Yokota et al., Leukemia. 1997 11:1605-1609).

An example of tumor cells that express FLT3-ITD is the MV4,11 cell line (Lange et al., Blood, 1987, 70:192-199). The methods to evaluate the potency FLT3 receptor inhibitors to induce tumor regression using mouse xenograft models expressing a mutated form of FLT3 have been described (O'Farrell et al., Blood 2003, 101: 3597-3605), in particular on pages 3600 and 3601.

As an illustration of said characterization of the upper limit of the desired daily dosage range per human adult through Method 2 as described above, example of sunitinib may be taken.

The minimum inhibiting dose inducing maximal tumor regression is 20 mg/kg for sunitinib given by oral gavage in the mouse model mentioned above (O'Farrell et al., Blood, 2003, 101-3597-3605).

The HED value may be determined by the following operation:

HED=20/12.3(allometric FDA factor for the mouse)
*60=98 mg.

It may here been specified that it is not surprising that an allometric calculation gives a result that is two times greater than the recommended dose, because the allometric factor is an approximation generalized for all drugs, based on the normalization of doses to body surface area, which is the standard way to approximate equivalent exposure if no further information is available (US Food and Drug Administration's Guidance for Industry—Estimating the Maximum Safe Starting Dose in Initial Clinical Trials for Therapeutics in Adult Healthy Volunteers, July 2005). Thus, this approximation does not take into account the individual pharmacokinetics properties of each drug.

HED/4=24.5 mg.

As in the case of sunitinib, when the HED/4 value determined by Method 1, and Method 2 differs, the daily dosage of the FLT3 inhibitor to treat neuropathic pain and chronic pain with a neuropathic component will be based on the value determined in Method 1, because this value is obtained in the clinical setting and not affected by the approximation mentioned above.

Various active doses for treating human cancer and doses in the mouse for tumor regression are gathered herein after in table 1.

TABLE 1

| FLT3 inhibitor receptor | Active dose for treating cancer (by cancer type) | Corresponding reference for clinical dose | minimum inhibiting dose inducing maximal tumor regression (mg/kg) | Corresponding reference for xenograft model |
|---|---|---|---|---|
| Sunitinib (SU-11248) | For GIST and RCC: 50 mg and for pNET: 37.5 mg | FDA label, EMA SmPC | 20 | O'Farrell et al., Blood 2003, 101: 3597-3605 |
| Lestaurtinib (CEP-701) | 80 for AML | Knapper et al., Blood 2006, 108: 3262-3270 | | |
| Midostaurin (PKC412, CGP-41251) | 50 twice a day for AML | Gallogy & Lazarus, J Blood Med 2016, 7: 73-83 | 100 | Weisberg et al., Cancer Cell 2002, 1: 433-443 |
| Gilteritinib | 80 | Thom, Future Oncol. (2015) 11(18), 2499-2501 | >3 | Ueno et al., Blood 2016 128: 2830 |
| Semaxinib (SU-5416) | 145 mg/m² = 235 mg for a human with a body weight of 60 kg for advanced or recurrent head and neck cancers; | Fury et al., Invest New Drugs (2007) 25: 165-172 | | |
| Linifanib (ABT-869) | 15 for AML | Wang et al., Leukemia & Lymphoma, 53: 8, 1543-1551, | 20 | Shankar et al., Blood. 2007, 109: 3400-3408) |
| Fostamatinib | 100-200 twice a day | Flinn et al., European Journal of Cancer 54 (2016) 11e17 | | |
| Pexidartinib | 1000 | NCT02371369 available at www.clinicaltrials.gov | | |
| Sorafenib | 400 twice a day for RCC, Hepatocellular carcinoma and differentiated thyroid carcinoma | FDA label | 10 | Auclair et al., Leukemia 2007, 21: 439-445 |
| Cabozantinib | 60 for RCC | FDA label | | |
| Ponatinib | 45 for chronic myeloid leukemia or acute lymphoblastic leukemia | FDA label | 25 | Gozgit et al., Mol Cancer Ther; 10(6); 1028-35. |
| Ilorasertib (ABT-348) | 540 mg once weekly and 480 mg twice weekly for acute myelogenous leukaemia, myelodysplastic syndrome or chronic myelomonocytic leukaemia | Garcia-Manero et al., Invest New Drugs. 2015, 33: 870-880 | 20 | Glaser et al., J Pharmacol Exp Ther. 2012, 343: 617-627 |
| Pacritinib (ONX-0803, SB-1518) | 200 twice daily or 400 once daily | NCT02055781 available at www.clinicaltrials.gov | | |

TABLE 1-continued

| FLT3 inhibitor receptor | Active dose for treating cancer (by cancer type) | Corresponding reference for clinical dose | minimum inhibiting dose inducing maximal tumor regression (mg/kg) | Corresponding reference for xenograft model |
|---|---|---|---|---|
| Famitinib | 25 for gastroenteropancreatic neuroendocrine tumor | NCT01994213 available at www.clinicaltrials.gov | | |
| Pexidartinib (PLX-3397) | 200 | NCT02371369 available at www.clinicaltrials.gov | | |
| Quizartinib (AC220) | 30 for AML | Ostronoff & Estey, Expert Opin. Investig. Drugs 2013, 22: 1659-1669 | 10 | Chao et al., J Med Chem 2009, 52: 7808-7816 |

According to a more particular embodiment of the present invention, the upper limit of the daily dosage range per human adult of FLT3 receptor inhibitor is the daily dose per human adult of FLT3 receptor inhibitor for the treatment of cancer as defined above divided by 6, in particular divided by 10.

According to a further more particular embodiment of the present invention, the lower limit of the daily dosage range per human adult of FLT3 receptor inhibitor is the higher value between the lower limit defined in method 1, step (iii) and the daily dose per human adult of FLT3 receptor inhibitor for the treatment of cancer as defined above divided by 100, in particular divided by 75, more particularly divided by 50.

According to said calculation method, implementing Methods 1 and 2 as described above, according to the present invention, when the FLT3 receptor inhibitor is sunitinib, the daily dosage per human adult per day ranges from 0.5 (50 mg/100) to 12.5 (50 mg/4) per human adult, in particular from 0.67 (50 mg/75) to 7.3 (method 1) mg and more particularly from 1 (50 mg/50) to 3.6 mg (method 1) per human adult.

According to another particular embodiment of the present invention, implementing Methods 1 and 2 as described above, when the FLT3 receptor inhibitor is quizartinib:
(i) According to Method 1, the maximal inhibition on the SNL model in rat is 0.77 mg/kg and the HED is 0.77/6.2*60=7.5 mg. The lower limit is the greater value between HED/20=0.37 mg and 0.001 mg, i.e. 0.37 mg and the upper limit is the lower value between HED*20=149 mg and 50 mg, i.e. 50 mg. The daily dosage per day per human for quizartinib for the treatment of neuropathic pain and chronic pain comprising a neuropathic component ranges from 0.37 mg to 50 mg.
(ii) According to Method 2, the daily dosage per human adult per day ranges from 0.3 mg (1/100 of the highest active dose in cancer, which is 30 mg) to 7.5 mg (1/4 the highest active dose in cancer) per human adult, in particular from 0.4 mg (1/75 of the highest active dose in cancer) to 5 mg (1/6 of the highest active dose in cancer) and more particularly from 0.6 mg (1/50 of the highest active dose in cancer) to 3 mg (1/10 of the highest active dose in cancer) per human adult.

According to another particular embodiment of the present invention, implementing methods 1 and 2 as described above, when the FLT3 receptor inhibitor is gilteritinib:

(i) According to Method 1, the maximal inhibition on the SNL model in rat is 2 mg/kg and the HED is 2/6.2*60=19.4 mg. The lower limit is the greater value between HED/20=0.97 mg and 0.001 mg, i.e. 0.97 mg and the upper limit is the lower value between HED*20=388 mg and 50 mg, i.e. 50 mg. The daily dosage per day per human for gilteritinib for the treatment of neuropathic pain and chronic pain comprising a neuropathic component ranges from 0.97 mg to 50 mg.

(ii) According to Method 2, the dosage per human adult given twice daily ranges from 0.8 mg (1/100 of the highest active dose in cancer, which is 80 mg) to the lowest dose between 20 mg (1/4 the active dose in cancer) and 50 mg, i.e. 20 mg per human adult, in particular from 1.1 mg (1/75 of the active dose in cancer) to the lowest dose between 80 mg/6 and 50 mg, i.e. 50 mg, and more particularly from 8 mg (1/50 the active dose in cancer) to 40 mg (1/10 the active dose in cancer) per human adult.

According to another particular embodiment of the present invention, implementing Methods 1 and 2 as described above, when the FLT3 receptor inhibitor is midostaurin:

(i) According to Method 1, the maximal inhibition on the SNL model in rat is 4 mg/kg and the HED is 4/6.2*60=39 mg. The lower limit is the greater value between HED/20=1.9 mg and 0.001 mg, i.e. 1.9 mg and the upper limit is the lower value between HED*20=774 mg and 50 mg, i.e. 50 mg. The daily dosage per day per human for quizartinib for the treatment of neuropathic pain and chronic pain comprising a neuropathic component ranges from 1.9 mg to 50 mg.

(ii) According to Method 2, the dosage per human adult given twice daily ranges from 0.5 mg (1/100 of the highest active dose in cancer) to 12.5 mg (1/4 the active dose in cancer) per human adult, in particular from 0.67 mg (1/75 of the highest active dose in cancer) to 8.3 mg (1/6 the active dose in cancer) and more particularly from 1 mg (1/50) to 5 mg (1/10 the active dose in cancer) per human adult.

The dosage range calculation may thus be summarized in the following table 2.

Sunitinib:

| | Method 1<br>HED = 0.73 mg | | Method 2<br>Cancer dose (CD) = 50 mg | | |
|---|---|---|---|---|---|
| Level | Lower limit | Upper limit | Lower limit | Upper limit | Range |
| 1 | HED/20 = 0.037 | HED * 20 = 14.6 | CD/100 = 0.5 | CD/4 = 12.5 | 0.5-12.5 |
| 2 | HED/10 = 0.073 | HED * 10 = 7.3 | CD/75 = 0.67 | CD/6 = 8.3 | 0.67-7.3 |
| 3 | HED/5 = 0.15 | HED * 5 = 3.6 | CD/50 = 1 | CD/10 = 5 | 1-3.6 |

Quizartinib:

| | Method 1<br>HED = 7.5 mg | | Method 2<br>Cancer dose (CD) = 30 mg | | |
|---|---|---|---|---|---|
| Level | Lower limit | Upper limit | Lower limit | Upper limit | Range |
| 1 | HED/20 = 0.37 | HED * 20 = 149 | CD/100 = 0.3 | CD/4 = 7.5 | 0.37-7.5 |
| 2 | HED/10 = 0.75 | HED * 10 = 75 | CD/75 = 0.4 | CD/6 = 5 | 0.75-5 |
| 3 | HED/5 = 1.5 | HED * 5 = 45 | CD/50 = 0.6 | CD/10 = 3 | 1.5-3 |

Gilteritinib:

| | Method 1<br>HED = 19.4 mg | | Method 2<br>Cancer dose (CD) = 80 | | |
|---|---|---|---|---|---|
| Level | Lower limit | Upper limit | Lower limit | Upper limit | Range |
| 1 | HED/20 = 0.97 | HED * 20 = 1160 | CD/100 = 0.8 | CD/4 = 20 | 0.97-20 |
| 2 | HED/10 = 1.9 | HED * 10 = 580 | CD/75 = 1.1 | CD/6 = 13.3 | 1.9-13.3 |
| 3 | HED/5 = 3.9 | HED * 5 = 290 | CD/50 = 1.6 | CD/10 = 8 | 3.9-8 |

Midostaurine:

| | Method 1<br>HED = 39 mg | | Method 2<br>Cancer dose (CD) = 50 | | |
|---|---|---|---|---|---|
| Level | Lower limit | Upper limit | Lower limit | Upper limit | Range |
| 1 | HED/20 = 2.0 | HED * 20 = 780 | CD/100 = 0.5 | CD/4 = 12.5 | 2.0-12.5 |
| 2 | HED/10 = 3.9 | HED * 10 = 390 | CD/75 = 0.67 | CD/6 = 8.3 | 3.9-8.3 |
| 3 | HED/5 = 1.8 | HED * 5 = 195 | CD/50 = 1 | CD/10 = 5 | 1-5 |

Such a very low amount of FLT3 receptor inhibitors allows to attenuate neuropathic pain or the neuropathic component of a chronic pain as explained above, and even to suppress it. Still due to this low dosage, the pharmaceutical compositions containing it are safe as far as all adverse effects that are associated with the use of said FLT3 receptor inhibitors at anti-cancer doses are attenuated, and even avoided.

The invention further relates to a method for the treatment of neuropathic pain and chronic pain comprising a neuropathic component, the method comprising the step of administering to a patient in need thereof a FLT3 receptor inhibitor as mentioned above, wherein the daily dosage range per human adult per day of said FLT3 receptor inhibitor consists of a dosage range determined by a method comprising the steps of:

(i) determining the minimal inhibiting dose of said FLT3 receptor inhibitor that induces the maximal inhibition of mechanical pain hypersensitivity in a model of nerve injury, which is the Spinal Nerve Ligation (SNL) Model in rats, (ii) converting said dose to the Human Equivalent Dose (HED) by the allometric correction method, the daily dose being calculated as the daily dose for a human with a body weight of 60 kg, and (iii) establishing a daily dosage range per human adult per day wherein (iii-1) the lower limit of the said daily dosage range per human adult per day is the greater value between HED/20 determined via the SNL rat model and 0.001 mg, and (iii-2) the upper limit of the said daily dosage range is the lower value between HED*20 determined via the SNL rat model and 50 mg.

According to one embodiment, the FLT3 receptor inhibitor is administered as a once a day, or a twice a day, a three times a day, or three times a week formulation.

All combinations of doses, frequencies and treatment period are encompassed within the scope of the present invention, provided that the daily dosage per human adult is fulfills the requirement of the claimed invention.

It will be understood that the daily dosage of the FLT3 receptor inhibitor will also be decided by the attending physician within the scope of sound medical judgment. The specific therapeutically effective dose level for any particular patient will also depend upon a variety of factors including the disorder being treated and the severity of the disorder; activity of the specific compound employed, the specific composition employed, the age, body weight, general health, sex and diet of the patient; the time of administration, route of administration, and rate of excretion of the specific compound employed; the duration of the treatment, drugs used in combination or coincidental with the FLT3 receptor inhibitor employed; and like factors well known in the medical arts.

According to a particular embodiment, sunitinib may be administered at various dosages and regimen provided that the daily dosage per human adult fulfills the requirement of the claimed invention, and in particular once a day at doses ranging from 0.5 to 12.5 mg, in particular from 0.67 to 7.3 mg, more particularly from 1 to 3.6 mg. According to a further particular embodiment, quizartinib may be administered at various dosages and regimen provided that the daily dosage per human adult fulfills the requirement of the claimed invention, and in particular once a day at doses ranging from 0.37 to 7.5 mg, in particular from 0.75 to 5 mg, more particularly from 1.5 to 3 mg.

According to a further particular embodiment, gilteritinib may be administered at various dosages and regimen provided that the daily dosage per human adult fulfills the requirement of the claimed invention, and in particular once a day at doses ranging from 0.97 to 20 mg, in particular from 1.9 to 13.3 mg, more particularly from 3.9 to 8 mg. According to a further particular embodiment, midostaurin may be administered at various dosages and regimen provided that the daily dosage per human adult fulfills the requirement of the claimed invention, and in particular once a day at doses ranging from 2 to 12.5 mg, in particular from 3.9 to 8.3 mg, more particularly from 1 to 5 mg.

The pharmaceutical composition may also contain another drug for the treatment of neuropathic pain, well known to the man skilled in the art, in combination with a FLT3 receptor inhibitor according to the present invention.

The FLT3 receptor inhibitor of the invention may thus be used in combination with other therapeutically active agents, for instance, inhibitors of receptor tyrosine kinase (RTK) class III or RTK class VII inhibitors. RTK class III (Platelet-derived Growth factor (PDGF) receptor family) is a class of receptor tyrosine kinases including c-KIT and c-fms. RTK class VII (Tropomyosin-receptor-kinase (Trk) receptor family) is a class of receptor tyrosine kinases including TrkA, TrkB and TrkC. The foregoing therapeutically active agents are listed by way of example and are not meant to be limiting. Accordingly, The FLT3 receptor inhibitor of the invention may thus be used in combination with one or more therapeutically active agents selected in the group consisting of class III RTK inhibitors or class VII RTK inhibitors.

Formulations

A FLT3 receptor inhibitor according to the present invention may be implemented within pharmaceutical composition that may contain an effective amount of said FLT3 receptor inhibitor, and one or more pharmaceutical excipients.

The aforementioned excipients are selected according to the dosage form and the desired mode of administration.

A pharmaceutically acceptable carrier or excipient refers to a non-toxic solid, semi-solid or liquid filler, diluent, encapsulating material or formulation auxiliary of any type.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions.

Any route of administration may be used. For example, a FLT3 receptor inhibitor can be administered by oral, parenteral, intravenous, transdermal, intramuscular, rectal, sublingual, mucosal, nasal, or other means. In addition, a FLT3 receptor inhibitor can be administered in a form of pharmaceutical composition and/or unit dosage form.

According to one embodiment, the FLT3 receptor inhibitor is dedicated to oral administration and in particular formulated within tablets (including rapid dissolving and delayed release tablets), gel capsules, syrups, powders, granules and oral suspensions or solutions, sublingual or buccal administration forms.

According to a further embodiment, the FLT3 receptor inhibitor is dedicated to topical administration, in particular formulated as a gel or a skin patch.

According to a said particular embodiment, the said FLT3 receptor inhibitor may also be administered under the form of a free base or a pharmaceutically acceptable salt, as described above.

Topical formulations in the framework of the present invention include gel or transdermal formulations, skin patches or transdermal delivery patches.

A skin patch or transdermal delivery patch may or not comprise a matrix layer which may for example be a solid or semi-solid layer. Any polymeric matrix may for example be employed, so long as the patch is capable of delivering the FLT3 receptor inhibitor and relieving neuropathic pain and/or chronic pain over the desired time period.

The transdermal delivery patch may further comprise further layers.

A person skilled in the art of the invention would appreciate what are suitable excipients for inclusion in said patch or transdermal delivery patch. Some examples include, but are not limited to, solvents, thickeners or gelling agents, preservatives, surfactants, stabilizers, buffers, emollients, colors, fragrances, and appearance modifiers.

A gel or transdermal formulation of the present application may comprise penetration enhancers known in the art, for example, ethoxydiglycol (transcutanol), dimethyl isosorbide and mixtures thereof. Said gel or transdermal formulation of the present invention may comprise a thickening agent.

The examples below according to the invention are given as illustrations with no limiting nature.

EXAMPLES

Example 1: Effects of Sunitinib on Inflammatory Pain 1.1. Materials & Methods

Animals:

Adult mice (8-10 week-old) (Janvier LABS, Le Genest Saint-Isle, France) were used according to the guidelines of the International Association for the Study of Pain. Mice were housed in cages with a 12/12 hr light/dark cycle and fed food and water ad libitum. Behavioral responsiveness of the animals was tested following ten days of habituation to the testing environment and the observer. Before testing, mice were acclimatized for 60 min in the temperature and light-controlled testing room within a plastic cylinder or on wire mesh.

A 0.6 g-von Frey filament was used for measuring punctuate hindpaw mechanical hypersensitivity with the dynamic plantar aesthesiometer (Bioseb, France). Sharp withdrawal of the stimulated hindpaw was considered as a positive response. The procedure was applied 10 times and the percentage of positive responses was calculated. Basal positive responses were recorded twice during two, consecutive days.

Inflammatory pain was produced by local injection of Complete Freund's Adjuvant (CFA), which induces a prolonged swelling that becomes maximal at 24 hrs and persists for at least 7 days (Iadarola et al., Pain. 1988; 35:313-26). After anaesthesia under isoflurane, CFA (20 µl) was injected subcutaneously into the metatarsal region of the left hindpaw (just proximal to the distal calluses) almost parallel to the footpad. Mechanical hypersensitivity was measured 4 days later. Sunitinib (5 or 20 mg/kg) was administered and mechanical hypersensitivity was measured 1 and 2 days after the sunitinib administration.

Statistics:
Results are presented as mean±S.E.M.

1.2 Results

FIG. 1 depicts the results of said example 1. Four days after the CFA injection, animals display mechanical hypersensitivity which is shown by the increase in the percentage of withdrawal after mechanical stimulation. The administration of sunitinib, an FLT3 inhibitor, did not reduce mechanical hypersensitivity, demonstrating that FLT3 inhibition does not affect inflammatory pain.

Example 2: Effects of Sunitinib on Capsaicin-Induced Increase of Extracellular Calcium in Dorsal Root Ganglia (DRG)

2.1. Materials & Methods
DRG Neurons Primary Culture:
Primary neuronal cultures were established from lumbar (L4 to L6) dorsal root ganglia (DRG) of adult mice as previously described (Boudes et al, J. Neurosci. 29, 46, 10060-10068). Ganglia were treated twice with collagenase A (1 mg/ml, Roche Diagnostic, France) for 45 minutes (37° C.) and then with trypsin-EDTA (0.25%, Sigma, St Quentin Fallavier, France) for 30 minutes. They were mechanically dissociated by passing 8 to 10 times through the tip of a fire-polished Pasteur pipette in neurobasal (Life Technologies, Cergy Pontoise, France) culture medium supplemented with 10% foetal bovine serum and DNase (50 U/ml, Sigma, St Quentin Fallavier, France). Isolated cells were collected by centrifugation and suspended in neurobasal culture medium supplemented with 2% B27 (Life Technologies), 2 mM glutamine, penicillin/streptomycin (20 U/ml, 0.2 mg/ml). Dissociated neurons were plated on poly-D,L-ornithine (0.5 mg/ml)-laminin (5 µg/ml)-coated glass coverslips at a density of 2500 neurons per well and were incubated in an incubator with a humidified 95% air/5% CO2 atmosphere. Two hours after plating, the culture medium was carefully removed and replaced to eliminate dead cells and tissue debris. The cells were maintained in culture at 37° C. until experiments are performed.

Measurements of Intracellular $Ca^{2+}$ ($[Ca^{2+}]_i$)

For intracellular $Ca^{2+}$ measurements, DRG neurons were used 18-30 h after plating as described previously. The cells were loaded with a Lock solution containing 2.5 µM Fura2—AM (Molecular probes, Invitrogen, France) by incubation at 37° C. for 30 minutes. The loading solution was washed three times and the Fura2-AM was left to de-esterified for 20 minutes at 37° C. During $[Ca^{2+}]_i$ measurements, perfusion rate of the cells was controlled with a gravity flow system, and the temperature was maintained at 37° C. using an in-line heating system (Warner Instruments). Drugs were delivered with a rapid-switching local perfusion system. Cells were imaged with an inverted microscope equipped with a NEOFLUAR 25×0.8 objective lens (Axiovert 200, Zeiss, Le Pecq, France) and a CCD camera (Cool SNAP ES, Roper Scientific, France). Lambda DG-4 filter changer (Sutter Instrument, Novato, Calif., USA) was used for switching between 340 nm and 380 nm excitation wavelengths. A Fura filter cube with 400 long pass dichroic and D510/40m emission band pass was used to collect fluorescence emissions separately for each wavelength. Images were acquired and analyzed with Metafluor software (Molecular Devices). Changes in intracellular calcium concentrations ($[Ca^{2+}]_i$) were monitored as changes of the ratio of the fura-2-fluorescence intensity recorded at 340 nm and 380 nm excitation wavelengths ($\Delta F_{340/380}$).

Only cells with a robust response to high $K^+$ application (50 mM) at the end of the protocol and a peak response to capsaicin (100 µM)>0.2 $\Delta F_{340/380}$ were retained. $[Ca^{2+}]_i$ peak response was easily distinguished from optical noise (<0.02 $\Delta F_{340/380}$). Capsaicin at 100 µM elicited a response >0.2 $\Delta F_{340/380}$ from the maximal number of cells and response magnitudes decreased with subsequent agonist presentation as previously described (Bonnington, J. K., and McNaughton, J. Physiol. 551, 433-446). Each neuron was stimulated three times by capsaicin at 4-5 30 min interval. $[Ca^{2+}]_i$ response peak and area data are presented as the ratio of post-FL capsaicin response to the second naïve capsaicin response in individual cells (ΔFpeak, ΔFarea). Response areas were calculated as a measure of total $[Ca^{2+}]_i$ influx. The portion of the calcium response that was used for this measurement included the entire curve from the initiation of the response until the point at which the calcium signal returned to the prestimulus baseline. Typically, this occurred in <120 S.

Unless otherwise stated, ail standard chemicals were purchased from Sigma (France) except FL (from ABCYS SA, Paris, France). They were dissolved or conditioned in double distilled water or DMSO or in ethanol according to the recommendations suggested in the Merck Index-13th edition or recommendations from the suppliers. The osmolarity of all the solutions ranged between 298 and 303 mosmol/l.

Statistics:
Results are presented as mean±S.E.M. For comparison between the two groups, the data were analyzed by two-way ANOVA, and if warranted, followed t tests using the computer program Prism (GraphPad, San Diego, Calif.). A P value <0.05 was considered statistically significant.

2.2. Results

Figure 2:
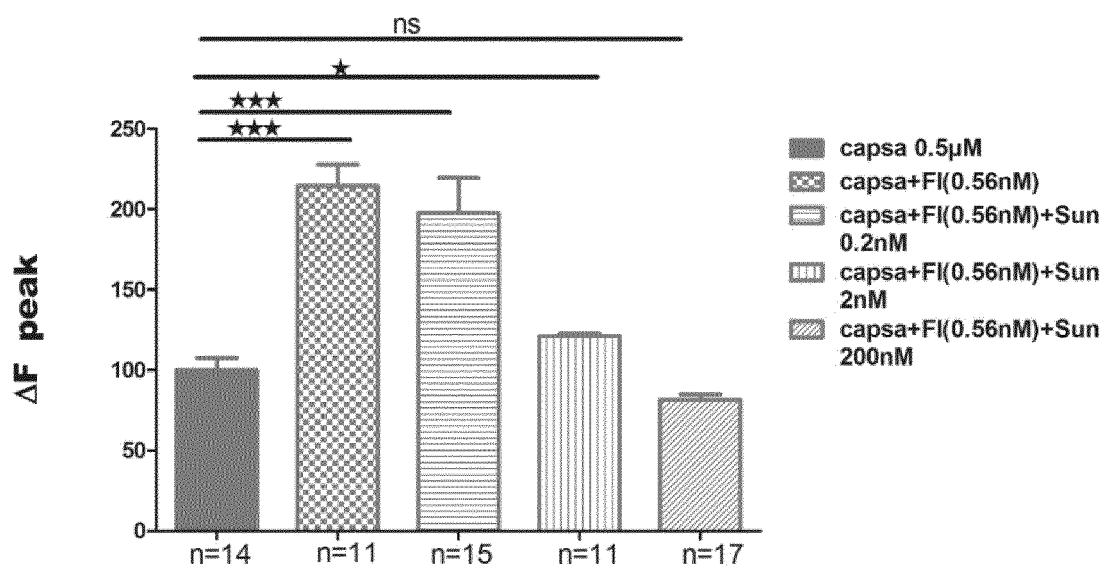
FIG. 2 represents the inhibition of capsaicin response by the FLT3 inhibitor sunitinib in native sensory neuronal cells culture as illustrated in example 2.

FIG. 2 depicts the results of said example 2. The response is expressed as the peak value of the variation of the calcium-associated fluorescence signal (ΔF peak)±S.E.M. The FLT3 ligand FL, at the concentration of 0.56 nM potentiated the response to capsaicin (capsa) at the concentration of 0.5 µM. The response to FL was inhibited in a concentration dependent manner by sunitinib (Sun). *P<0.05; P<0.01; *P<0.001 by the Mann-Whitney U test.

As shown in FIG. 2, FL at the concentration of 0.56 nM elicited a potentiation of the $[Ca^{2+}]_i$ peak response to capsaicin (0.5 µM). This potentiation of the capsaicin response was inhibited by sunitinib in a concentration-dependent manner. The $IC_{50}$ value of the effect of sunitinib was calculated by non-linear regression analysis to be 0.70 nM.

Example 3: Effects of the FLT3 Receptor Inhibitor Sunitinib on Nerve Injury-Induced Mechanical Pain Hypersensitivity in Rat 3.1. Materials & Methods
Spinal Nerve Ligation (SNL) Surgery in Rats:
Adult Sprague Dawley rats (300-340 gr) (Janvier LABS, Le Genest Saint-Isle, France) were used according to the guidelines of the International Association for the Study of Pain. Rats were housed in cages with a 12/12 hr light/dark cycle and fed food and water ad libitum. Behavioral responsiveness of the rats was tested following ten days of habituation to the testing environment and the observer. Left side L5 spinal nerve was injured as described by Kim and Chung (1992) Pain 50, 355-363. Anesthesia was induced and maintained with isoflurane. A midline incision was made at the L3-S2 level and the dorsal vertebral column from L4 to S2 was exposed. Part of the L6 transverse process was carefully removed with fine rongeurs. The L5 spinal nerve were isolated and tightly ligated distal to the DRG with a 4-0 silk suture. The wound was closed in two layers using absorbable sutures. A similar procedure was performed for the sham surgery, except that spinal nerve was not isolated and not ligated. After surgery, the posture of the sham-operated and SNL rats was closely monitored before they were used in different experiments.

Paw Pressure Test:

Mechanical hyperalgesia was measured as the threshold to a noxious mechanical stimulus. Nociceptive thresholds (NT) were determined in handled rats by a modification of the Randall-Selitto method (Kayser et al., Brain Res 1990; 508:329-332). Briefly, a constantly increasing pressure is applied to the rat hind paw until vocalization occurs. A Basile analgesimeter (Apelex, Massy, France; stylus tip diameter, 1 mm) was used. A 600-g cut-off value was determined to prevent tissue damage. The paw pressure was measured 24 hours after sunitinib oral administration.

Chemical:

Sunitinib was purchased from Sigma-Aldrich. It was administered by oral gavage at different doses in a volume of 1 ml/kg body weight in a solution of dimethylsulfoxide (DMSO) at 3%. Control animals received an equal volume of DMSO 3%.

Statistics:

The data are presented as means±SEM. One-way ANOVA was used to assess individual group comparisons. When a significant effect was observed, post-hoc analyses were performed using the Dunnett's test for comparison with the control group. The Newman-Keuls test was used for multiple comparisons between groups.

3.2. Results

The response effects to a fixed dose of sunitinib was established on nerve injury-induced mechanical pain hypersensitivity in rat (SNL model). Oral administration of sunitinib at 0.15 mg/kg reversed the mechanical hypersensitivity induced by nerve injury (FIG. 3). Conversely, intraperitoneal injection of vehicle had no effect on paw withdrawal responses to mechanical stimulation.

Figure 4:
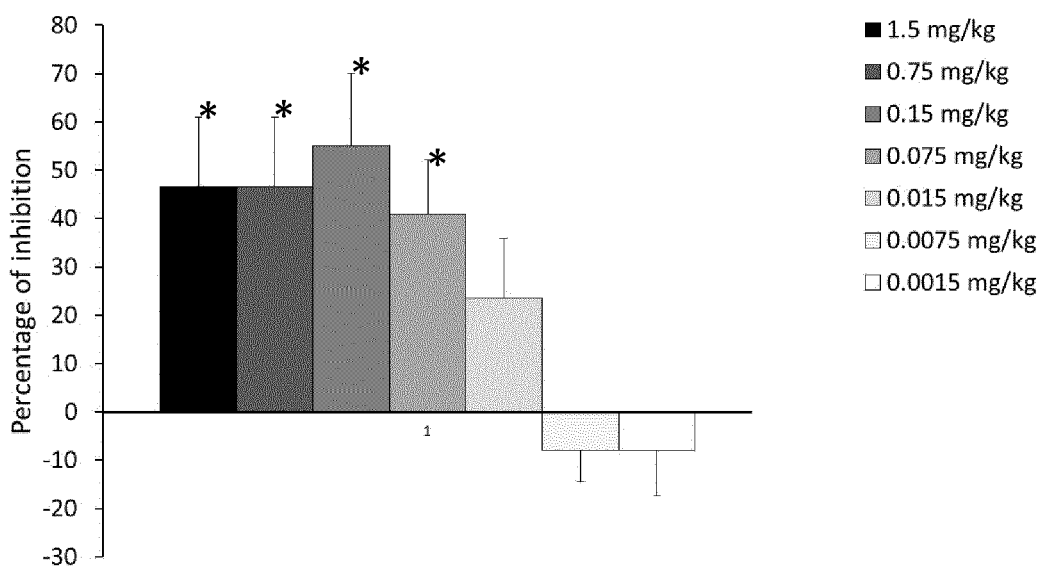
FIG. 4 depicts the inhibition of decrease in paw pressure threshold after sunitinib administered at increasing doses in rat (SNL model) as performed in example 3.

The response to increasing doses of sunitinib was then established. Maximal inhibition was obtained with sunitinib doses as low as 0.075 mg/kg, corresponding to the minimal dose for maximal inhibition of pain sensitivity (FIG. 4). The inhibiting dose giving 50% of inhibition ($ID_{50}$) value of sunitinib inhibition of SNL-induced mechanical hypersensitivity was calculated to 0.015 mg/kg (FIG. 4).

The invention claimed is:

1. A method for the treatment of neuropathic pain and chronic pain in which neuropathic pain coexists with a type of pain different from neuropathic pain, the method comprising the step of administering to a patient in need thereof a FLT3 receptor inhibitor, wherein the daily dosage range per human adult per day of said FLT3 receptor inhibitor consists of a dosage range determined by a method comprising the steps of:
(i) determining the minimal inhibiting dose of said FLT3 receptor inhibitor that induces the maximal inhibition of mechanical pain hypersensitivity in a model of nerve injury, which is the Spinal Nerve Ligation Model in rats,
(ii) converting said dose to the Human Equivalent Dose (HED) by the allometric correction method, the daily dose being calculated as the daily dose for a human with a body weight of 60 kg, and
(iii) establishing a daily dosage range per human adult per day wherein the lower limit of the said daily dosage range per human adult per day is the greater value between HED/20 determined via a rat model and 0.001 mg and the upper limit of the said daily dosage range is the lower value between HED*20 determined via a rat model and 50 mg.

2. The method according to claim 1, wherein the lower limit of the said daily dosage range per human adult per day is the greater value between HED/10 and 0.002 mg and the upper limit of the said daily dosage range is the lower value between HED*10 and 25 mg.

3. The method according to claim 1, wherein the lower limit of the said daily dosage range per human adult per day is the greater value between HED/5 and 0.0025 mg and the upper limit of the said daily dosage range is the lower value between HED*5 and 20 mg.

4. The method according to claim 1, wherein said FLT3 receptor inhibitor is sunitinib and the daily dosage per human adult per day ranges from 0.037 to 14.6 mg per human adult.

5. The method according to claim 1, wherein said FLT3 receptor inhibitor is sunitinib and the daily dosage per human adult per day ranges from 0.15 mg to 3.6 mg per human adult.

6. The method according to claim 1, wherein the upper limit of the said daily dosage range per human adult per day of the said FLT3 receptor inhibitor is the lower value between the upper limit as determined in claim 1 and one of
(a) a quarter of the active daily dosage per human adult of the said FLT3 receptor inhibitor for the treatment of a cancer selected from gastrointestinal stromal tumor, metastatic renal cell carcinoma, and acute myeloid leukemia, or
(b) a quarter of the daily dose per human adult of the said FLT3 receptor inhibitor for the treatment of cancer, said daily dose being determined by a method comprising the steps of:
(i) determining the minimum inhibiting dose inducing maximal tumor regression in a mouse xenograft model sensitive to FLT3 inhibition, and
(ii) converting said dose to the Human Equivalent Dose (HED) by the allometric correction method, the daily dose being calculated as the daily dose for a human with a body weight of 60 kg.

7. The method according to claim 6, wherein the upper limit of the daily dosage range per human adult of FLT3 receptor inhibitor is the daily dose per adult of FLT3 receptor inhibitor for the treatment of cancer as defined in claim 6 divided by 6.

8. The method according to claim 6, wherein the upper limit of the daily dosage range per human adult of FLT3 receptor inhibitor is the daily dose per adult of FLT3 receptor inhibitor for the treatment of cancer as defined in claim 6 divided by 10.

9. The method according to claim 6, wherein the lower limit of the daily dosage range per human adult of FLT3 receptor inhibitor is the daily dose per human adult of FLT3 receptor inhibitor for the treatment of cancer as defined in claim 6 divided by 100.

10. The method according to claim 6, wherein the lower limit of the daily dosage range per human adult of FLT3 receptor inhibitor is the daily dose per human adult of FLT3 receptor inhibitor for the treatment of cancer as defined in claim 6 divided by 50.

11. The method according to claim 1, wherein the chronic pain is selected from low-back pain, osteoarthritic pain, cancer pain, sciatica.

12. The method according to claim 1, wherein said FLT3 receptor inhibitor is selected from AG1295 and AG1296; Lestaurtinib; CEP-5214 and CEP-7055; CHIR-258; GTP; Midostaurin; gilteritinib; semaxinib; linifanib; fostamatinib; pexidartinib; sorafenib; cabozantinib; ponatinib; pacritinib; pexidartinib; famitinib; MLN-608; MLN-518; MLN-608; sunitinib; SU-11657; SU-5416 and SU-5614; THRX-165724; AMI-10706; VX-528 and VX-680; XL 999; quizartinib and a mixture thereof.

13. The method according to claim 1, wherein said FLT3 receptor inhibitor is selected from sunitinib, quizartinib, gilterinitinib and midostaurin.

14. The method according to claim 1, wherein said FLT3 receptor inhibitor is sunitinib and the daily dosage per human adult ranges from 0.5 to 12.5 mg.

15. The method according to claim 1, wherein said FLT3 receptor inhibitor is sunitinib and the daily dosage per human adult ranges from 1 to 3.6 mg.

16. The method according to claim 1, wherein said FLT3 receptor inhibitor is quizartinib and the daily dosage per human adult ranges from 0.37 to 7.5 mg.

17. The method according to claim 1, wherein said FLT3 receptor inhibitor is quizartinib and the daily dosage per human adult ranges from 1.5 to 3 mg.

18. The method according to claim 1, wherein said FLT3 receptor inhibitor is gilteritinib and the daily dosage per human adult ranges from 0.97 to 20 mg.

19. The method according to claim 1, wherein said FLT3 receptor inhibitor is gilteritinib and the daily dosage per human adult ranges from 3.9 to 8 mg.

20. The method according to claim 1, wherein said FLT3 receptor inhibitor is midostaurin and the daily dosage per human adult ranges from 2 to 12.5 mg.

21. The method according to claim 1, wherein said FLT3 receptor inhibitor is midostaurin and the daily dosage per human adult ranges from 1 to 5 mg.

22. The method according to claim 1, wherein the said inhibitor is administered under the form of a free base or a pharmaceutically acceptable addition salt thereof.

23. The method according to claim 1, wherein the FLT3 receptor inhibitor is administered as a once a day, or a twice a day, a three times a day, or a three times a week formulation.

24. The method according to claim 1, wherein the FLT3 receptor inhibitor is dedicated to oral administration.

25. The method according to claim 1, wherein the FLT3 receptor inhibitor is dedicated to oral administration formulated within tablets including rapid dissolving and delayed release tablets, gel capsules, syrups, powders, granules and oral suspensions or solutions, sublingual or buccal administration forms.

26. The method according to claim 1, wherein the FLT3 receptor inhibitor is dedicated to topic administration.

27. The method according to claim 1, wherein the FLT3 receptor inhibitor is dedicated to topic administration formulated within gel or skin patch.

28. The method according to claim 1, wherein the neuropathic pain is selected from pain arising from metabolic diseases, infectious diseases, trigeminal neuralgia, post-traumatic neuropathic pain, lumbosacral radiculopathic pain, post-chirurgical neuropathic pain, iatrogenic neuropathic pain, and central neuropathic pain.

29. The method according to claim 28, wherein the neuropathic pain is selected from painful diabetic neuropathic pain, post-herpetic neuralgia and chemotherapy-based neuropathic pain.

* * * * *